United States Patent [19]
Gildersleeve et al.

[11] Patent Number: 5,527,268
[45] Date of Patent: *Jun. 18, 1996

[54] ORTHOPEDIC KNEE BRACE AND ASSOCIATED KNEE CONDYLE PAD

[75] Inventors: Richard E. Gildersleeve, Escondido; Keith L. Cassford, San Diego; Theodore V. Tillinghast, III, Carlsbad, all of Calif.

[73] Assignee: Smith & Nephew Donjoy Inc., Carlsbad, Calif.

[*] Notice: The term of this patent shall not extend beyond the expiration date of Pat. No. 5,316,547.

[21] Appl. No.: 246,972

[22] Filed: May 19, 1994

Related U.S. Application Data

[63] Continuation-in-part of Ser. No. 907,160, Jul. 1, 1992, Pat. No. 5,316,547, Ser. No. 104,184, Aug. 10, 1993, Pat. No. 5,415,625, Ser. No. 191,410, Feb. 3, 1994, Pat. No. 5,458,565, and Ser. No. 199,091, Feb. 22, 1994, abandoned, which is a continuation-in-part of Ser. No. 191,410, Feb. 3, 1994, Pat. No. 5,458,565, said Ser. No. 104,184, is a continuation-in-part of Ser. No. 907,160, Jul. 1, 1992, Pat. No. 5,316,547, said Ser. No. 191,410, is a continuation-in-part of Ser. No. 104,184, Aug. 10, 1993, Pat. No. 5,415,625.

[51] Int. Cl.$^6$ ............................................. A61F 5/00
[52] U.S. Cl. ........................ 602/26; 602/16; 602/13
[58] Field of Search .................... 602/5, 13, 16, 602/23, 26

[56] References Cited

U.S. PATENT DOCUMENTS

| | | |
|---|---|---|
| 2,531,074 | 11/1950 | Miller . |
| 3,581,741 | 6/1971 | Rosman . |
| 3,902,482 | 9/1975 | Taylor . |
| 3,945,047 | 3/1976 | Jarrell, Jr. . |
| 3,955,565 | 5/1976 | Johnson, Jr. . |
| 3,958,569 | 5/1976 | Vosburgh . |
| 4,201,203 | 5/1980 | Applegate . |
| 4,219,892 | 9/1980 | Rigdon . |
| 4,280,489 | 7/1981 | Johnson, Jr. . |
| 4,287,920 | 9/1981 | Johnson, Jr. . |
| 4,378,009 | 3/1983 | Rowley et al. . |
| 4,567,887 | 2/1986 | Couch, Jr. ............................. 602/13 X |
| 4,624,247 | 11/1986 | Ford . |
| 4,628,954 | 12/1986 | Johnson, Jr. . |
| 4,632,098 | 12/1986 | Grundei et al. . |
| 4,634,176 | 2/1987 | Mason et al. . |
| 4,667,672 | 5/1987 | Romanowski . |
| 4,703,750 | 11/1987 | Sebastian et al. . |
| 4,777,946 | 10/1988 | Watanabe et al. . |

(List continued on next page.)

FOREIGN PATENT DOCUMENTS

| | | | |
|---|---|---|---|
| 2627381 | 8/1989 | France . | |
| 2136294 | 9/1984 | United Kingdom | .............. A61F 5/01 |

OTHER PUBLICATIONS

Generation II Orthotics USA Inc., *Osteoarthritis Pain–Free Mobility*, 1993, USA.
Omni Scientific, Inc., *Radiograph Engineered Custom Bracing*, 1993, USA.

*Primary Examiner*—Linda C. Dvorak
*Attorney, Agent, or Firm*—Brown, Martin Haller & McClain

[57] ABSTRACT

A hinged orthopedic knee brace has a structural frame and at least one knee condyle pad attachable thereto. The frame has a plurality of rigid or stiffened support components dynamically connected by one or more hinges. The knee condyle pad is attachable to the frame proximal to the hinge and is configured to conform to the surface of the body overlying the lateral or medial knee condyle. The knee condyle pad has a fluid-containing primary bladder with a loop configuration encircling a depressed interior opening of the pad. The primary bladder is sized to circumscribe the periphery of the knee condyle and the interior opening is sized to receive the apex of the knee condyle. The distal portion of the primary bladder has a reduced volume and reduced surface area relative to the proximal portion thereof. Accordingly, the distal portion of the pad avoids excessive pressure, and the pain associated therewith, on the peroneal nerve and fibular head proximal to the knee condyle, while effectively gripping the knee condyle and simultaneously cushioning the knee condyle from the frame.

29 Claims, 3 Drawing Sheets

U.S. PATENT DOCUMENTS

| | | |
|---|---|---|
| 4,821,707 | 4/1989 | Audette . |
| 4,870,956 | 10/1989 | Fatool et al. . |
| 4,872,448 | 10/1989 | Johnson, Jr. . |
| 4,938,207 | 7/1990 | Vargo . |
| 4,999,932 | 3/1991 | Grim . |
| 5,002,045 | 3/1991 | Spademan . |
| 5,022,391 | 6/1991 | Weidenburner . |
| 5,025,575 | 6/1991 | Lakic . |
| 5,025,782 | 6/1991 | Salerno . |
| 5,042,464 | 8/1991 | Skwor et al. . |
| 5,078,128 | 1/1992 | Grim et al. . |
| 5,088,478 | 2/1992 | Grim . |
| 5,107,823 | 4/1992 | Fratesi . |
| 5,113,599 | 5/1992 | Cohen et al. . |
| 5,125,400 | 6/1992 | Johnson, Jr. . |
| 5,158,767 | 10/1992 | Cohen et al. . |
| 5,186,163 | 2/1993 | Dye . |
| 5,230,695 | 7/1993 | Silver et al. . |
| 5,277,698 | 1/1994 | Taylor . |

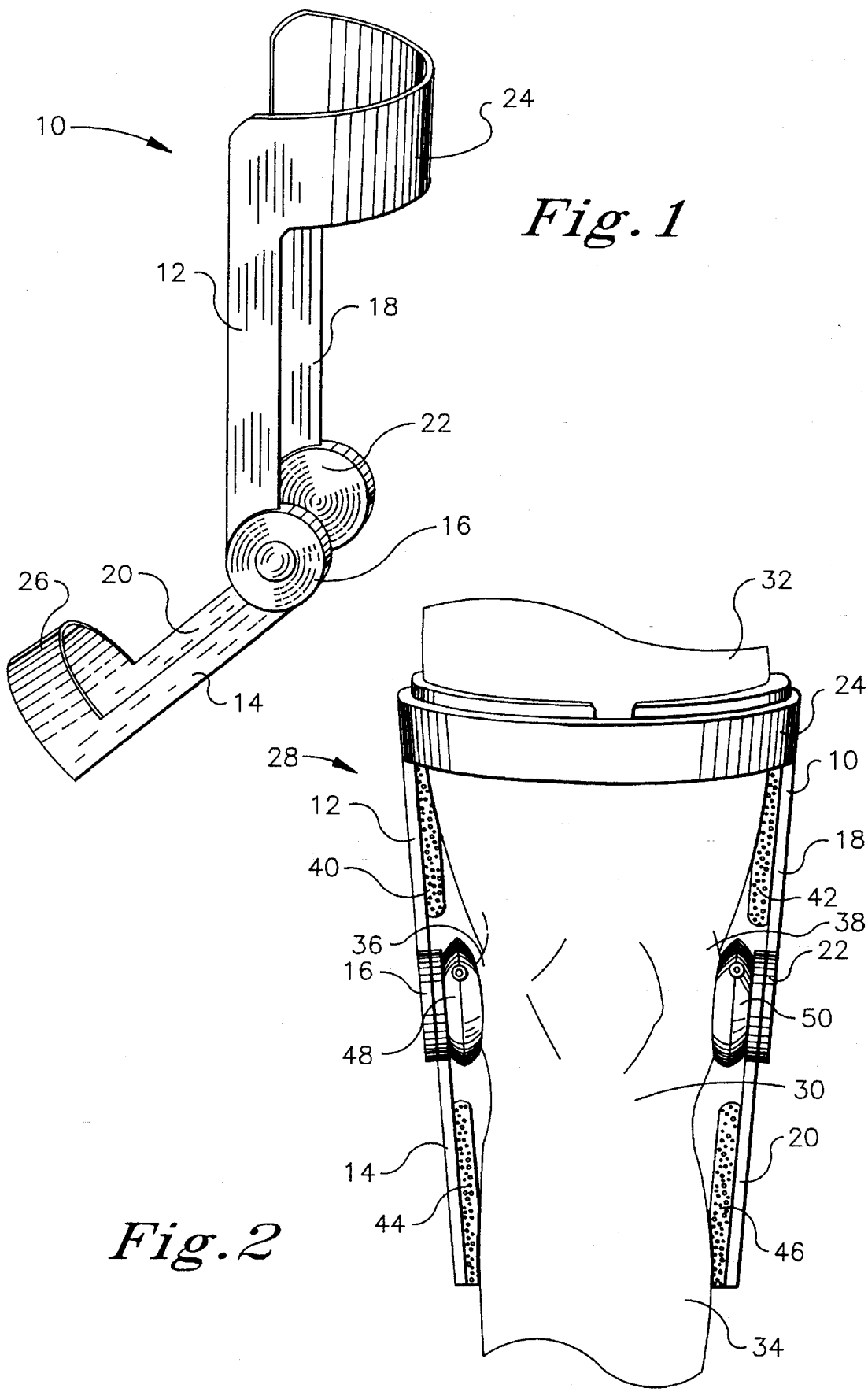

ORTHOPEDIC KNEE BRACE AND ASSOCIATED KNEE CONDYLE PAD

This is a continuation-in-part patent application of a patent application Ser. No. 07/907,160 filed on Jul. 1, 1992 now U.S. Pat. No. 5,316,547. This application is also a continuation-in-part patent application of a patent application Ser. No. 08/104,184 filed on Aug. 10, 1993, now U.S. Pat. No. 5,415,625 which is a continuation-in-part patent application of patent application Ser. No. 07/907,160.

This application is also a continuation-in-part patent application of a patent application Ser. No. 08/191,410 filed on Feb. 3, 1994 now U.S. Pat. No. 5,458,565 which is a continuation-in-part patent application of patent application Ser. No. 08/104,184, now U.S. Pat. No. 5,415,625. This application is also a continuation-in-part patent application of a patent application Ser. No. 08/199,091 filed on Feb. 22, 1994, now abandoned, which is a continuation-in-part patent application of patent application Ser. No. 08/191,410.

TECHNICAL FIELD

The present invention relates generally to orthopedic braces, and particularly to an orthopedic brace and a pad attachable thereto for supporting the brace against the body of a user. More particularly, though not exclusively, the present invention relates to an orthopedic knee brace and a fluid-containing pad attachable thereto for supporting the brace against the knee condyle of a user.

BACKGROUND OF THE INVENTION

Hinged orthopedic braces are commonly employed to stabilize a skeletal joint of a user when the joint has been weakened by injury or other infirmity. The brace typically has a structural frame that is made up of a plurality of rigid or stiffened support components dynamically linked together by one or more hinges to support the joint during user activity. The frame is mounted on the body of a user such that the hinges traverse the joint being stabilized, while the support components are secured to the body by a system of pliant straps. Pads are generally attached to the inside faces of the support components to cushion the contact points between the frame and user's body and to provide a stable base of support for the brace against the user's body.

Foam is often used as the pliant padding material because of the ability of foam to conform to the body of the user. Despite the presence of foam pads, however, the user often experiences discomfort from painful point loads while wearing the brace because of the high compression forces the frame applies to the body at certain contact points during physical activity. Conventional foam pads are either overly compressive or overly stiff, diminishing there cushioning effect. Lightweight foams have not been found which are adequately compressive for the comfort of the user, yet which are sufficiently firm to provide a stable base of support for the brace against the body of the user.

It has been observed that point loads on the lateral knee condyle resulting from hinged knee braces are particularly troublesome. During active use of the brace, there is significant contact between the hinge region of the brace frame and the knee condyles. The lateral knee condyle is especially sensitive to contact because of the presence of the peroneal nerve and fibular head. U.S. Pat. 3,581,741 discloses a hinged knee brace having a foam pad positioned between the upper support member of the brace and the medial knee condyle that is configured in the shape of a doughnut to reduce the point load on the medial knee condyle. The doughnut-shaped foam pad taught therein, however, is unsatisfactory for lateral knee condyle applications because the pad has a continuous peripheral surface that painfully impinges against the fibular head and peroneal nerve at the distal end of the pad when the pad is positioned on the lateral knee condyle.

Accordingly, it is an object of the present invention to provide an orthopedic brace having a structural frame that can be secured to the body of a user with both a high degree of stable support and a high degree of user comfort. It is a further object of the present invention to provide a lightweight pad attachable to the frame of an associated orthopedic brace that comfortably stabilizes the frame against the body of the user by dynamically conforming to and firmly gripping the contours of the body while fully cushioning the body contours from the rigid or stiffened support components of the frame. It is yet another object of the present invention to provide a knee condyle pad attachable to the frame of an orthopedic knee brace that comfortably stabilizes the frame against the body of the user without applying undue pressure to the knee condyle, and specifically without inducing significant pain in the fibular head or peroneal nerve proximal to the lateral knee condyle.

SUMMARY OF THE INVENTION

In accordance with one embodiment, the present invention is a hinged orthopedic brace having a structural frame and one or more pads attached thereto that provide secure and comfortable support for the brace when the frame is mounted on the body of a user. The frame comprises a plurality of rigid or stiffened support components and one or more hinges dynamically connecting the support components. Each pad comprises a fluid-containing primary bladder formed from a flexible skin that is shaped into a containment configuration to enclose a quantity of fluid therein. The primary bladder is provided with a selectively openable and closeable fluid port for the selective injection of fluid into the bladder or the selective withdrawal of fluid from the bladder. Alternatively, the quantity of fluid is substantially permanently sealed within the primary bladder.

The present embodiment is particularly applicable to an orthopedic knee brace mountable on the leg of a user to stabilize the knee joint by restricting the motion thereof. The brace comprises a structural frame made up of a hinge and a plurality of substantially rigid or stiffened upper and lower support components. The upper support components are engagable with the upper leg above the knee joint and the lower support components are engagable with the lower leg below the knee joint. The hinge is positionable at the knee joint and rotatably connects the upper and lower support components to pivot them about the hinge in correspondence with flexion and extension of the knee joint as permitted by the brace. The brace further comprises a knee condyle pad attached to the inside face of the hinge, providing a stable base of support for the brace against the leg of the user. The knee condyle pad also cushions the lateral or medial knee condyle from the hinge or associated support components of the frame and diminishes point loads to the knee condyle when the brace is mounted on the leg of the user.

In another embodiment, the present invention is a specifically configured knee condyle pad attachable to the above-described structural frame of an orthopedic knee brace. The knee condyle pad is configured to conform to the surface of the body overlying the lateral or medial knee condyle. The knee condyle pad comprises a fluid-containing primary bladder having a loop configuration with an interior opening. The primary bladder is sized such that it circumscribes the periphery of the condyle. A fluid-containing secondary bladder having a considerably smaller volume than the primary bladder occupies the interior opening and receives the apex of the condyle. Alternatively, a void space or a continuous sheet or laminate of planar material occupies the interior opening.

The loop configuration is a closed curve, having the interior opening offset from the center of the bladder toward the distal portion thereof. Alternatively, the loop configuration of the bladder is a partially opened curve having, in addition to the interior opening, a peripheral opening positioned in the distal portion of the bladder that is continuous with the interior opening. In either case, the loop configuration of the bladder provides the distal portion of the bladder with a reduced volume and reduced surface area relative to the proximal portion thereof. Accordingly, the distal portion of the pad avoids excessive pressure, and the pain associated therewith, on the peroneal nerve and fibular head proximal to the lateral knee condyle, while effectively gripping the knee condyle and simultaneously cushioning the knee condyle from the frame.

The construct of the knee condyle pad includes two sheets of an elastically deformable skin with one overlying the other. The sheets are joined together by at least one seam that defines the configuration of the bladder and seals the interior of the bladder from the external environment. The bladder may be provided with a selectively sealable port through the skin that enables selective fluid communication between the interior of the bladder and the external environment for adding fluid to the bladder or releasing fluid from the bladder, respectively. The pad may further be provided with a pliant facing that is affixed to the outside of one sheet and with a pliant backing that is affixed to the outside of the other sheet. The facing provides a soft, absorbent surface for engagement with the user's body and the backing provides added cushion between the bladder and the support components of the frame. The backing is preferably formed from a hook component or a loop component of a conventional fabric hook and loop fastener coupling, with the remaining component of the fabric coupling being positioned on the inside face of the hinge, facilitating removable attachment of the pad to the brace frame.

The present invention will be further understood, both as to its structure and operation, from the accompanying drawings, taken in conjunction with the accompanying description, in which similar reference characters refer to similar parts.

BRIEF DESCRIPTION OF THE DRAWINGS

FIG. 1 is a perspective view of a structural frame for a knee brace of the present invention.

FIG. 2 is a frontal view of the knee brace of the present invention in place on the leg of a user.

DESCRIPTION OF PREFERRED EMBODIMENTS

Figure 3:
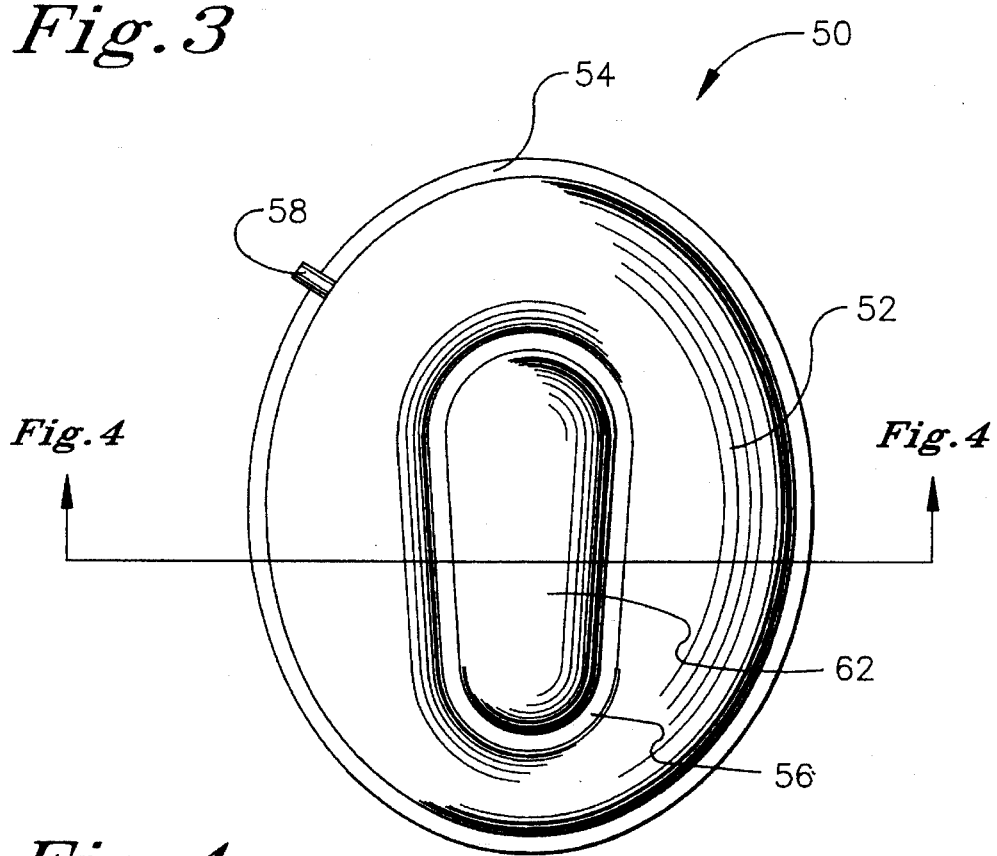
FIG. 3 is a plan view of a knee condyle pad of the present invention attachable to the knee brace of FIG. 2.

Referring initially to FIG. 1, a structural frame for an orthopedic knee brace of the present invention is generally designated 10. The frame 10, shown by way of example, is a conventional design having a plurality of rigid or stiffened support components including medial upper and lower arms 12, 14, a medial hinge plate 16, lateral upper and lower arms 18, 20, a lateral hinge plate 22, an upper leg cuff 24, and a lower leg cuff 26. The term "stiffened" as used herein refers to a component that is somewhat more flexible than a rigid component, yet is sufficiently stiff to cause the user discomfort when positioned against the body during periods of prolonged activity. The upper and lower leg cuffs 24, 26 have a curved shape providing them with concave inner faces, while the medial and lateral hinge plates 16, 22, the medial upper and lower arms 12, 14, and the lateral upper and lower arms 18, 20 are generally straighter providing them with relatively flatter inner faces.

In practice, the upper support components 12, 18, 24 can be integrally formed in a unitary structure from a high-strength material, such as a plastic, metal or composite. The lower support components 14, 20, 26 can likewise be integrally formed in a unitary structure from similar materials. The hinge plates 16, 22 are generally defined as the rigid or stiffened portion of the frame 10 integral with or proximal to the rotary hinge mechanism, such as the external housing of the rotary hinge mechanism shown herein. Portions of the arms 12, 14, 18, 20 proximal to the hinge mechanism, or other proximal components integrally functioning with the hinge mechanism can also be included within the term "hinge plates" as defined herein.

Referring to FIG. 2, an orthopedic knee brace of the present invention, having the above-described structural frame 10, is generally designated 28. The knee brace 28 is shown operably positioned on the left leg 30 of a user, wherein the support components of the frame 10 engage the leg 30 at a plurality of contact points. In particular, support of the brace 28 against the leg 30 is provided by engagement of the inner faces of the medial and lateral upper arms 12, 18 and upper leg cuff 24 with the upper leg 32 and engagement of inner faces of the medial and lateral lower arms 14, 20 and lower leg cuff 26 (obscured from view in FIG. 2) with the lower leg 34. Support of the brace 28 against the leg 30 is further provided by engagement of the inner face of the medial hinge plate 16 with the medial knee condyle 36 and engagement of the inner face of the lateral hinge plate 22 with the lateral knee condyle 38.

To facilitate conforming engagement of the frame support components with the leg 30, while simultaneously promoting the comfort of the user, the orthopedic knee brace 28 is provided with a plurality of fluid-containing pads that removably attach to the inner faces of the frame 10 at the points of compression contact with the leg 30. In particular, a medial upper support pad 40 is attached to the inner faces of the medial upper arm 12 and upper leg cuff 24. A lateral upper support pad 42, that is substantially a mirror image of the medial upper support pad 40, is attached to the inner faces of the lateral upper arm 18 and upper leg cuff 24. The upper support pads 40, 42 reside in compression between the upper leg 32 and frame 10 when the frame 10 engages the upper leg 32 as shown. Medial and lateral lower support pads 44, 46 substantially similar to the upper support pads 40, 42 are attached to the inner faces of the medial and lateral lower arms 14, 20 and lower leg cuff 26, respectively, to reside in compression between the lower leg 34 and the frame 10 when the frame 10 engages the lower leg 34. The specific configuration of the upper and lower support pads 40, 42, 44, 46 shown herein is described in U.S. patent application Ser. No. 08/104,184, incorporated herein by reference. Alternate configurations of the upper and lower support pads having utility with the brace 28 of the present invention are described in U.S. patent application Ser. No. 07/907,160, incorporated herein by reference.

The brace 28 is further provided with fluid-containing medial and lateral knee condyle pads 48, 50. The medial knee condyle pad 48 is attached to the inner face of the medial hinge plate 16 to reside in compression between the medial knee condyle 36 and the medial hinge plate 16 when the plate 16 engages the medial knee condyle 36. The lateral knee condyle pad 50 is substantially a mirror image of the medial knee condyle pad 48 and is attached to the inner face of the lateral hinge plate 22 to reside in compression between the lateral knee condyle 38 and the lateral hinge plate 22 when the plate 22 engages the lateral knee condyle 38.

Although not shown in FIG. 2, the brace 28 is also provided with a plurality of adjustable pliant straps engaging the arms 12, 14, 18, 20 and wrapping around the leg 30. The configuration and placement of the straps is conventional and well known to the skilled artisan. The straps secure the frame 10 to the leg 30 of the user by increasing the compression force at the contact points between the frame 10 and leg 30. It is further noted that the present orthopedic knee brace 28 has been described above as positioned on the left leg 30. It is understood by the skilled artisan, however, that the brace 28 is readily adaptable for positioning on the right leg as well within the scope of the present invention.

Figure 4:
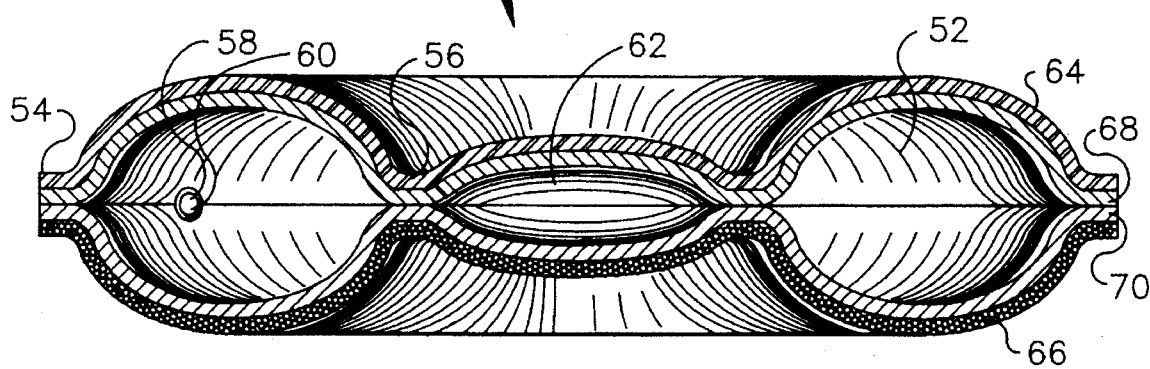
FIG. 4 is a cross-sectional view of the knee condyle pad of FIG. 3 as seen along line 4—4.

The configuration and construction of the knee condyle pads 48 and 50 are described hereafter with reference to FIGS. 3–7. Referring initially to FIGS. 3 and 4, a first embodiment of a lateral knee condyle pad 50 is shown to comprise a fluid-containing, closed-curve primary bladder 52 having an outer plan perimeter and an inner plan perimeter defined by a primary seam 54 and a secondary seam 56, respectively. The primary seam 54 continuously surrounds the primary bladder 52 following an oval-shaped, closed-loop pathway, thereby defining the entire peripheral outer plan perimeter of the primary bladder 52. The secondary seam 56 also follows a continuous, somewhat oval-shaped, closed-loop pathway and is encircled by the primary seam 54. The secondary seam 56, however, is centrally offset from the primary seam 54. The secondary seam 56 defines the inner plan perimeter of the primary bladder 52 and also defines the outer plan perimeter of an interior opening that is a depression substantially encircled by the primary bladder 52. The interior opening has a number of alternate configurations as described hereafter, but in all cases the interior opening is characterized as having a substantially lesser height or thickness than the primary bladder 52 when the lateral knee condyle pad 50 is in an uncompressed state.

The primary and secondary seams 54, 56 are fluid-tight to effectively seal the selected fluid contained within the interior of the primary bladder 52 from the external environment. The fluid contained within the primary bladder 52 is defined herein as a gas, a liquid, or a highly-deformable gel. The preferred fluid is a gas at ambient temperature, such as air. The fluid enables the uncompressed primary bladder 52 to retain a substantially irregular toroid shape. The configuration of the primary bladder 52 is termed "an irregular toroid" because its radial cross-section is not uniform about the entire rotation of the primary bladder 52 due to the off center position of the secondary seam 56.

A tubular port 58 having a selectively openable and closeable valve 60 positioned therein is provided through the primary bladder 52, and in particular through the primary seam 54, to enable selective fluid communication between the interior of the primary bladder 52 and the external environment. Accordingly, when the valve 60 is closed, there is substantially no fluid communication between the interior of the primary bladder 52 and the exterior. When the valve 60 is opened, fluid can be added to or withdrawn from the primary bladder 52 as desired to modify the volume of the primary bladder 52. As can be appreciated by the skilled artisan, the volume of the primary bladder 52 is modified to enhance the fit of the brace 28 against the leg 30 or to enhance the cushioning effect of the pad 50. The valve 60 is a duckbill valve or other conventional valve configured to receive the injection needle of a manual fluid pump through port 58.

In accordance with the embodiment of the lateral knee condyle pad 50 shown in FIGS. 3 and 4, the interior opening is occupied by a secondary bladder 62 that is in fluid isolation from the primary bladder 52. The plan perimeter of the secondary bladder 62 is defined by the secondary seam 56 and the secondary bladder 62 has a substantially continuous radial cross section. The secondary bladder 62 contains a lesser quantity of fluid than the primary bladder 52 and is substantially less thick than the primary bladder 52 when the lateral knee condyle pad 50 is in an uncompressed state. Unlike the primary bladder 52, the secondary bladder 62 is substantially permanently sealed, having no port therein, such that the quantity of fluid within the secondary bladder 62 is substantially constant throughout the life of the pad 50.

The primary and secondary seams 54, 56 of the lateral knee condyle pad 50 are configured such that the secondary bladder 62 is centrally offset from the primary bladder 52 toward the distal portion of the pad 50 that is radially opposite the proximal portion of the pad 50. The term "centrally offset" refers to the fact that the primary and secondary bladders 52, 62 do not share a common center. The terms "proximal" and "distal", as used in describing the pad 50, are relative to the midsection of the body of a user on which the orthopedic knee brace 28 is positioned. Accordingly, the plan width of the proximal portion of the primary bladder 52 is substantially greater than the plan width of the distal portion of the primary bladder 52, wherein the plan width is defined as the distance between the outer plan perimeter and the inner plan perimeter of the primary bladder 52, as shown in FIG. 3. Correspondingly, the distal portion of the primary bladder 52 has a substantially reduced volume and surface area relative to the proximal portion of the primary bladder. The present configuration of the lateral knee condyle pad effectively reduces excessive pressure on the peroneal nerve and fibular head, which are in the distal region of the lateral knee condyle 38 shown in FIG. 2.

Specifically referring to FIG. 4, the lateral knee condyle pad 50 is shown to have a laminar construction comprising a facing 64 and a backing 66. It is noted that the thickness of the laminate layers have been exaggerated for purposes of illustration. The facing 64 is a sheet of a soft, pliant, absorbent material, such as synthetic suede or chamois, anteriorly laminated to both the primary and secondary bladders 52, 62. The backing 66 is likewise a sheet of pliant material posteriorly laminated to the bladders 52, 62 in substantially the same manner as the facing 64. A preferred backing 66 is the loop component of a hook and loop fastener, commonly termed VELCRO, configured as a cloth patch. A cloth patch of the hook component (not shown) is similarly laminated to the inner face of the lateral hinge plate 22 opposite the backing 66. It is understood that the positions of the hook and loop components can alternatively be reversed such that the loop component is laminated to the inner face of the lateral hinge plate 22 and the hook component is laminated to the outside of the second sheet 64.

In a preferred construction of the lateral knee condyle pad 50, the primary and secondary bladders 52, 62 are shown in FIG. 4 to be integrally formed from two continuous sheets 68, 70 of a film-like skin. The skin is a highly-flexible, elastically-collapsible, fluid-impervious material such as a plastic, e.g., polyurethane or polyvinyl chloride. Construction of the lateral knee condyle pad 50 is initiated by laminating the facing 64 onto the outside of the first sheet 68 and correspondingly laminating the backing 66 onto the outside of the second sheet 70 by an adhesive such as a conventional glue. The bladders 52, 62 are then constructed by overlaying the first sheet 68 atop the second sheet 70. The primary seam 54 is formed by positioning the port 58 and enclosed valve 60 between the two sheets 68, 70 at the outer plan perimeter thereof and joining the sheets 68, 70 around the port 58 and along the continuous oval path of the outer plan perimeter using conventional means, such as radio frequency (r.f.) welding. The secondary seam 56 is formed in substantially the same manner as the primary seam 54, but absent the port, such that the secondary seam 56 is positioned off center from the primary seam 54 and encircled thereby.

It is noted that when the primary and secondary seams 54, 56 are formed, a quantity of fluid, typically ambient air, can be trapped within the interiors of the seams 54, 56. The fluid retained within the interior of the secondary seam 56 remains therein without the further addition or withdrawal of fluid for substantially the life of the pad. The fluid within the interior of the primary seam 54, however, can subsequently be supplemented by injecting additional fluid via the port 58 and valve 60 in the manner described above to achieve a desired increase in the thickness of the primary bladder 52. Consequently, the distance separating the first and second sheets 68, 70 within the primary bladder 52 is substantially greater than the distance of separation within the secondary bladder 62.

Although not shown, the lateral knee condyle pad 50 of FIG. 4 can alternately be configured by evacuating the secondary bladder 62 and laminating the inside of the first sheet 68 to the inside of the second sheet 70 across the entire interior opening. Thus, the secondary bladder is excluded from this embodiment and the interior opening is occupied by the resulting laminate comprising the first and second sheets 68, 70, facing 64, and backing 66.

Figure 5:
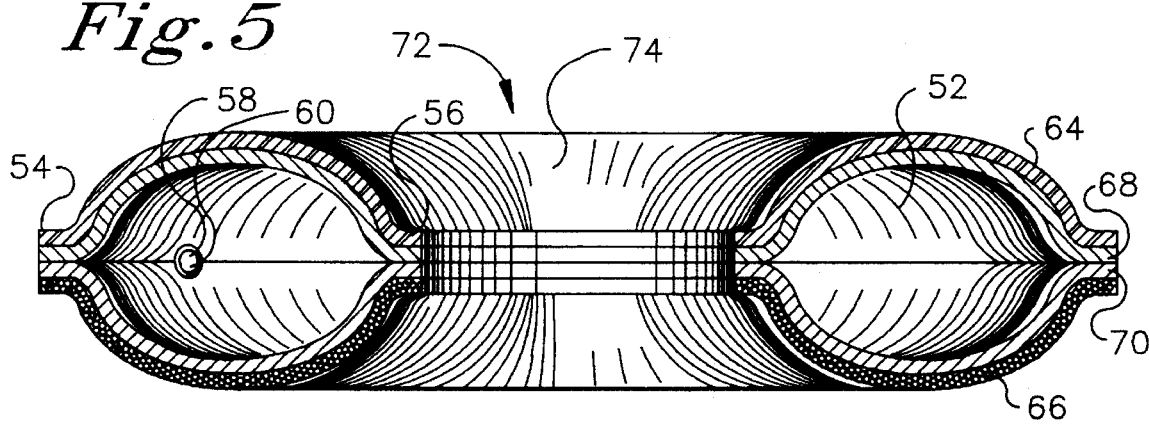
FIG. 5 is a cross-sectional view of an alternate knee condyle pad of the present invention attachable to the knee brace of FIG. 2.

Referring to FIG. 5 having substantially the same cross-sectional view as FIG. 4, another embodiment of a lateral knee condyle pad is shown and generally designated 72. Identical reference characters are used to identify elements common to both the lateral knee condyle pad 72 and the lateral knee condyle pad 50 insofar as the lateral knee condyle pad 72 is configured substantially the same as the lateral knee condyle pad 50 with the exception of the interior opening. The lateral knee condyle pad 72 excludes the secondary bladder from the interior opening and substitutes an interior void space 74 therefor. Accordingly, the pad 72 contains only one bladder, i.e., the primary bladder 52.

Figure 6:
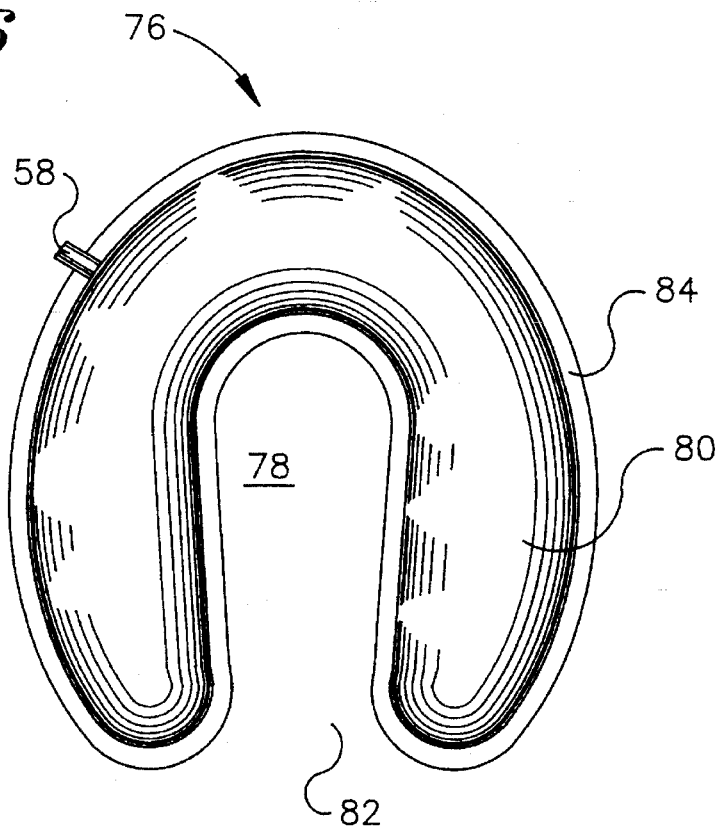
FIG. 6 is a plan view of another alternate knee condyle pad of the present invention attachable to the knee brace of FIG. 2.

Referring to FIG. 6, yet another embodiment of a lateral knee condyle pad is shown and generally designated 76. Identical reference characters are used to identify elements common to the above-described lateral knee condyle pads 50, 72 and the present embodiment of the lateral knee condyle pad 76. Like the lateral knee condyle pad 72, the lateral knee condyle pad 76 excludes the secondary bladder from the interior opening and substitutes an interior void space 78 therefor. The pad 76 also has a primary bladder 80 that is substantially toroid-shaped. The primary bladder 80, however, is a partially opened curve having a relatively limited peripheral opening in the distal portion thereof that is occupied by a peripheral void space 82 continuous with the interior void space 78. Accordingly, the lateral knee condyle pad 76 has a horseshoe-shaped plan perimeter defined by a single close-looped primary seam 84. Because of the peripheral void space 82, the interior void space 78 can be substantially concentric with the primary bladder 80, or alternatively centrally offset therefrom, without defeating the function of the pad 76 to alleviate pressure on the fibular head and peroneal nerve. It is also noted that the lateral knee condyle pad 76 has the same laminar construction as the above-described lateral knee condyle pads 50, 72, comprising two sheets of film-like skin, a facing, and a backing.

Figure 7:
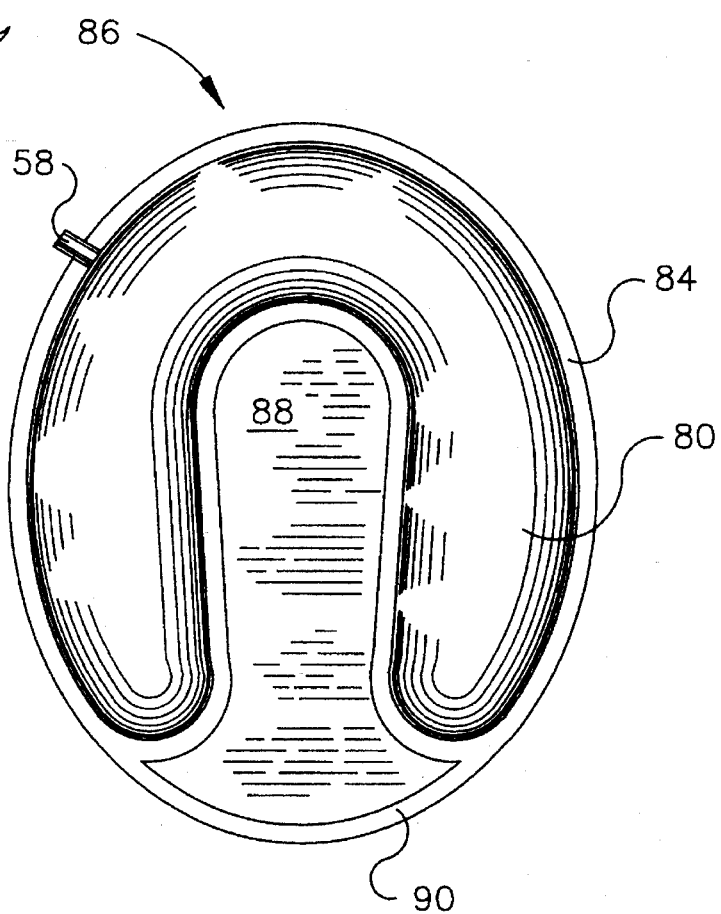
FIG. 7 is a plan view of yet another alternate knee condyle pad of the present invention attachable to the knee brace of FIG. 2.

Referring to FIG. 7, a further embodiment of a lateral knee condyle pad is shown and generally designated 86. Identical reference characters are used to identify elements common to the lateral knee condyle pads 50, 72, 76 and the lateral knee condyle pad 86. The lateral knee condyle pad 86 is configured substantially the same as the lateral knee condyle pad 76 with the exception of the peripheral and interior openings. In addition to the primary bladder 80 and primary seam 84, the lateral knee condyle pad 86 includes a secondary bladder 88 positioned within the peripheral and interior openings thereof and having a similar construction to the secondary bladder 62 of the lateral knee condyle pad 50 shown in FIGS. 3 and 4. The pad 86 also includes a secondary seam 90, extending across the distal plan perimeter of the secondary bladder 88 and having two ends intersecting the primary seam 84.

Although not shown, the lateral knee condyle pad 86 of FIG. 7 can alternately be configured by evacuating the secondary bladder 88 and laminating the insides of the two film-like sheets forming the secondary bladder 88 together across the entire peripheral and interior openings. Thus, the secondary bladder is excluded from this embodiment and the peripheral and interior openings are occupied by the resulting laminate comprising the two film-like sheets, a facing, and a backing.

Although only lateral knee condyle pads have been shown and described above, it is understood that the descriptions of the lateral knee condyle pads apply equally to medial knee condyle pads which are mirror images of the lateral knee condyle pads. It is also understood that other embodiments of knee condyle pads, in addition to those shown and described above, are possible within the scope of the present invention. For example, the present invention encompasses alternate embodiments of knee condyle pads that are substantially identical to the above-described embodiments, but which exclude the facing or backing from the pad, or which exclude the port and valve from the primary bladder of the pad. In accordance with those alternate embodiments of the pad excluding the port and valve from the primary bladder, a desired quantity of the selected fluid is initially charged to the primary bladder and substantially permanently sealed therein during construction of the pad. This substantially fixed fluid quantity is maintained within the primary bladder for the life of the pad. The selected fluid is preferably a gas at ambient temperature, such as air, sulfur hexafluoride, or a mixture thereof. The gas most preferably has a substantially higher molecular weight than air to reduce long-term leakage of gas through the skin of the primary bladder by diffusion.

The present invention further provides for alternate embodiments of knee condyle pads, wherein the primary bladder of the knee condyle pad does not have a toroid shape, but has substantially any shape defining a closed-curve or partially-opened curve loop that conforms to the perimeter of a knee condyle without excessively impinging on the fibular head and peroneal nerve and that provides an interior opening for receiving the apex of the knee condyle. Sufficient fluid is placed in the primary bladder to maintain the height of the primary bladder greater than the height of the knee condyle received therein during use of the brace to prevent substantial compressive contact of the knee condyle or peroneal nerve with the rigid or stiffened support components of the brace to which the pad is attached.

Alternative means for producing the knee condyle pad are also provided within the scope of the present invention. For example, the primary bladder can be formed from a single sheet of film-like material, rather than two sheets as disclosed above, by joining the edges of a single sheet together and welding the resulting joint, thus, forming a bladder sealed at the weld or welds. In other production alternatives, the primary bladder may be formed by blow molding or other conventional molding methods available to one skilled in the art.

While the foregoing preferred embodiments of the invention have been described and shown, it is understood that alternatives and modifications, such as those suggested and others, may be made thereto and fall within the scope of the present invention.

We claim:

1. An orthopedic knee brace positionable on the leg of a user comprising:

a hinge plate positionable opposite a knee condyle on the leg of the user adaptable to apply pressure to the knee condyle; and a fluid-containing primary bladder forming a substantially closed-curve loop encircling an interior opening, said primary bladder having a distal portion and a proximal portion radially opposite said distal portion, wherein the plan width of said distal portion is substantially less than the plan width of said proximal portion, and further wherein said primary bladder is positionable between said hinge plate and the knee condyle with said loop adaptable in size to circumscribe the knee condyle and said interior opening adaptable in size to receive a bony protrusion of the knee condyle, thereby alleviating pressure applied to the bony protrusion from said hinge plate.

2. An orthopedic knee brace as recited in claim 1 wherein said opening is depressed relative to said loop.

3. An orthopedic knee brace as recited in claim 1 further comprising means for selectively adding fluid to said primary bladder or withdrawing fluid from said primary bladder.

4. An orthopedic knee brace as recited in claim 1 further comprising a valve positioned in said primary bladder for selectively adding fluid to said primary bladder or withdrawing fluid from said primary bladder.

5. An orthopedic knee brace as recited in claim 1 wherein said primary bladder is formed substantially in the shape of a toroid.

6. An orthopedic knee brace as recited in claim 5 wherein the radial cross section of said primary bladder is nonuniform about the rotation of said bladder.

7. An orthopedic knee brace as recited in claim 1 wherein the volume of said distal portion of said primary bladder is substantially less than the volume of said proximal portion of said bladder.

8. An orthopedic knee brace as recited in claim 1 further comprising a secondary bladder positioned in fluid isolation from said primary bladder within said interior opening, wherein said secondary bladder is depressed relative to said primary bladder.

9. An orthopedic knee brace as recited in claim 1 wherein said interior opening is a void space.

10. An orthopedic knee brace as recited in claim 1 wherein said interior opening is centrally offset from said loop.

11. An orthopedic knee brace positionable on the leg of a user comprising:

a hinge plate positionable opposite a knee condyle on the leg of the user adaptable to apply pressure to the knee condyle; and a fluid-containing primary bladder forming a partially opened-curve loop having a peripheral opening, said loop partially encircling an interior opening, and said primary bladder having a distal portion and a proximal portion radially opposite said distal portion, wherein said peripheral opening is positioned at said distal portion of said primary bladder, and further wherein said primary bladder is positionable between said hinge plate and the knee condyle with said loop adaptable in size to circumscribe the knee condyle and said interior opening adaptable in size to receive a bony protrusion of the knee condyle, thereby alleviating pressure applied to the bony protrusion from said hinge plate.

12. An orthopedic knee brace as recited in claim 11 wherein the volume of said distal portion of said primary bladder is substantially less than the volume of said proximal portion of said bladder.

13. An orthopedic knee brace as recited in claim 11 further comprising a secondary bladder positioned in fluid isolation from said primary bladder within said interior opening, wherein said secondary bladder is depressed relative to said primary bladder.

14. An orthopedic knee brace as recited in claim 11 wherein said interior opening is a void space.

15. A knee condyle pad positionable on an orthopedic knee brace to support the brace against a knee condyle when the brace is mounted on the leg of a user, said knee condyle pad comprising:

a first sheet of an elastically deformable film;

a second sheet of an elastically deformable film overlaying said first sheet;

a primary seam sealingly joining said second sheet to said first sheet, thereby defining at least a portion of an outer plan perimeter of a primary bladder between said first and second sheets;

a secondary seam sealingly joining said second sheet to said first sheet, thereby defining at least a portion of an outer plan perimeter of a secondary bladder between said first and second sheets, wherein said secondary bladder is in fluid isolation from said first bladder, and further wherein said first bladder is formed substantially in the shape of a substantially closed-curve loop having an interior opening and said secondary bladder is positioned within said interior opening centrally offset from said loop; and a volume of fluid contained within said primary bladder, said volume of fluid sufficient to provide said primary bladder with a height greater than the height of said secondary bladder.

16. A knee condyle pad as recited in claim 15 further comprising a valve positioned in said primary bladder for selectively adding fluid to said primary bladder or withdrawing fluid from said primary bladder.

17. A knee condyle pad as recited in claim 15 wherein said primary bladder is formed substantially in the shape of a toroid.

18. A knee condyle pad as recited in claim 15 wherein the volume of said distal portion of said primary bladder is substantially less than the volume of said proximal portion of said bladder.

19. A knee condyle pad positionable on an orthopedic knee brace to support the brace against a knee condyle when the brace is mounted on the leg of a user, said knee condyle pad comprising:

a fluid-containing primary bladder forming a substantially closed-curve loop encircling an interior opening, said primary bladder having a distal portion and a proximal portion radially opposite said distal portion, wherein said interior opening is centrally offset from said loop in the direction of said distal portion, and further wherein said primary bladder is positionable between the brace and the knee condyle with said loop adaptable in size to circumscribe the knee condyle and said interior opening adaptable in size to receive a bony protrusion of the knee condyle, thereby alleviating pressure applied to the bony protrusion from the brace.

20. A knee condyle pad as recited in claim 19 further comprising a valve positioned in said primary bladder for selectively adding fluid to said primary bladder or withdrawing fluid from said primary bladder.

21. A knee condyle pad as recited in claim 19 wherein said primary bladder is formed substantially in the shape of a toroid.

22. A knee condyle pad as recited in claim 19 wherein the volume of said distal portion of said primary bladder is substantially less than the volume of said proximal portion of said bladder.

23. A knee condyle pad as recited in claim 19 further comprising a secondary bladder positioned in fluid isolation from said primary bladder within said interior opening, wherein said secondary bladder is depressed relative to said primary bladder.

24. A knee condyle pad as recited in claim 19 wherein said interior opening is a void space.

25. A knee condyle pad as recited in claim 19 wherein the plan width of said distal portion is substantially less than the plan width of said proximal portion.

26. A knee condyle pad positionable on an orthopedic knee brace to support the brace against a knee condyle when the brace is mounted on the leg of a user, said knee condyle pad comprising:

a fluid-containing primary bladder forming a partially opened-curve loop having a peripheral opening, said loop partially encircling an interior opening, and said primary bladder having a distal portion and a proximal portion radially opposite said distal portion, wherein said peripheral opening is positioned at said distal portion of said primary bladder, and further wherein said primary bladder is positionable between the brace and the knee condyle with said loop adaptable in size to circumscribe the knee condyle and said interior opening adaptable in size to receive a bony protrusion of the knee condyle, thereby alleviating pressure applied to the bony protrusion from the brace.

27. A knee condyle pad as recited in claim 26 wherein the volume of said distal portion of said primary bladder is substantially less than the volume of said proximal portion of said bladder.

28. A knee condyle pad as recited in claim 26 further comprising a secondary bladder positioned in fluid isolation from said primary bladder within said interior opening, wherein said secondary bladder is depressed relative to said primary bladder.

29. A hinged orthopedic brace positionable on a body of a user comprising:

a hinge plate positionable opposite a condyle on the body of the user;

a fluid-retaining bladder positionable between said hinge plate and the condyle, said bladder defining a loop with an interior opening, wherein said loop is adaptable in size to circumscribe the condyle and said opening is adaptable in size to receive the condyle; and a selectively sealable valve positioned in said bladder for selectively adding fluid to said bladder or withdrawing fluid from said bladder.

* * * * *